(12) United States Patent
Raymond-Coblantz

(10) Patent No.: US 8,986,752 B1
(45) Date of Patent: Mar. 24, 2015

(54) SKIN CARE TREATMENT

(71) Applicant: Sherry May Raymond-Coblantz, Bend, OR (US)

(72) Inventor: Sherry May Raymond-Coblantz, Bend, OR (US)

( * ) Notice: Subject to any disclaimer, the term of this patent is extended or adjusted under 35 U.S.C. 154(b) by 0 days.

(21) Appl. No.: 14/098,392

(22) Filed: Dec. 5, 2013

(51) Int. Cl.
| | | |
|---|---|---|
| *A61K 36/185* | (2006.01) | |
| *A61K 8/97* | (2006.01) | |
| *A61K 8/34* | (2006.01) | |
| *A61K 8/49* | (2006.01) | |
| *A61Q 19/00* | (2006.01) | |
| *A61Q 19/08* | (2006.01) | |

(52) U.S. Cl.
CPC . *A61K 8/97* (2013.01); *A61K 8/342* (2013.01); *A61K 8/498* (2013.01); *A61Q 19/007* (2013.01); *A61Q 19/08* (2013.01)
USPC .............................. 424/725; 424/774; 424/776

(58) Field of Classification Search
CPC ........... A61K 2300/00; A61K 2800/00; A61K 36/185
USPC .......................................... 424/725, 774, 776
See application file for complete search history.

(56) References Cited

U.S. PATENT DOCUMENTS

| | | | | |
|---|---|---|---|---|
| 2008/0279902 | A1* | 11/2008 | Luria et al. .................... | 424/401 |
| 2009/0068255 | A1* | 3/2009 | Yu et al. ........................ | 424/450 |
| 2013/0095196 | A1* | 4/2013 | Raymond-Coblantz ...... | 424/729 |

FOREIGN PATENT DOCUMENTS

| | | | | |
|---|---|---|---|---|
| CN | 101756830 | A | * | 6/2010 |
| CN | 103099756 | A | * | 5/2013 |
| CN | 103263371 | A | * | 8/2013 |
| CN | 103349641 | A | * | 10/2013 |
| DE | 20207155 | U1 | * | 9/2002 |
| FR | 002845594 | A1 | * | 4/2004 |
| JP | 2013006790 | A | * | 1/2013 |
| KR | 2012131971 | A | * | 12/2012 |
| RO | 116865 | B | * | 7/2001 |
| WO | WO 2006000196 | A1 | * | 1/2006 |

* cited by examiner

*Primary Examiner* — Chris R Tate
*Assistant Examiner* — Randall Winston
(74) *Attorney, Agent, or Firm* — Klarquist Sparkman, LLP.

(57) ABSTRACT

An organic skin moisturizer, which extends and improves the skin cells life cycle, comprised of Sea Buckthorn seed oil, Tamanu oil, Meadowfoam seed oil, Behenyl alcohol, Vetiver oil, Vitamin E or d-alpha tocopherol, Lecithin oil, Tea tree oil, *Helichrysum* oil, *Melissa* oil, and the titanium dioxide. The oils are blended together resulting in a compound that is easily applied to the skin for superior results to keep the skin cells healthier longer. This compound was created to address the Hayflick limit, which is that all skin cells can only divide a specific number of times before the skin cell dies.

1 Claim, No Drawings

SKIN CARE TREATMENT

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

The present invention relates to a composition for application on the skin for the treatment of wrinkled, damaged and dry skin. The composition has been found to be especially effective against skin blemishes, rosacea, eczema, wrinkles, dryness and contains properties of stimulation to tissue regeneration and epithelial healing with analgesic and anti-inflammation and anti-fungal effects but without leaving scars. The composition is a most welcome remedy for burn, cuts, frostbites, and sores. This anti-aging formula has been used to produce soft moist skin and can be used on an everyday basis without any negative affects on the skin or body. The composition promotes a firmness to the skin and dermal hydration.

There are many products and formulas for treating dry rough skin and just as many formulas to fight wrinkles. The prior art is replete with products and patents claiming skin protection and salvations for aging skin however the present invention combines a combination of organic ingredients for treating various skin disorders that is unique and effective in bringing about soft, moist skin and reducing wrinkles without harming the skin or the body.

Skin disorders, as the term is used herein, encompasses numerous skin conditions ranging in severity from severe dermatitis, severe dry skin, psoriasis, rosacea and other skin blemishes to less severe conditions, such as lack of adequate skin firmness, dermal hydration or scaling, which are nonetheless unsightly and may cause physical discomfort.

Until now, the treatment of skin disorders has been largely based on non-specific drugs, and only limited success has been achieved. Dermatitis, for example, which may be accompanied by severe scaling, fissures, edema, oozing, erosion, itching and thickening of the skin, commonly has been treated with corticosteroids. Such compounds provide symptomatic relief for some patients. Steroids, however, are known to produce many local and systemic side effects, and their long term use may not be desirable.

Similarly Vitamin D is therapeutically effective in treating certain skin disorders, but only in dosages which are associated with undesirable side effects. Vitamin D at the dose ranges used in currently marketed topical preparations is not therapeutically effective against contact dermatitis. Other formulations for treating skin disorders have either been ineffective or have caused significant irritation to the skin. Several formulations have been proposed to overcome the disadvantages of the prior art, both for treating skin disorders, and for use in cosmetics in order to prevent skin irritation and clear blemishes.

There are numerous patents issued for the care and condition of skin. Each patent uses a variety of ingredients with the combination providing some form of skin treatment. The list is exhaustive, and includes such patents as: U.S. Pat. No. 7,306,810 issued Dec. 11, 2007 to Spencer discloses a skin cream which comprises at least one anti-oxidant, an anti-inflammatory agent, an exfoliant, and an agent to protect against UV irradiation and the cream is made from either oils or creams to promote adsorption of the active ingredients and to increase vibrancy of the skin tone. U.S. Pat. No. 6,281,236 issued Aug. 28, 2001 to Farber discloses a skin cream composition containing allantoin and an emulsifier with improved stability coming from the adjustment of the pH to a range of 4.5 to 5.8. The lower pH preserves the stability of the allantoin and the functionality of the emulsifier system is maintained. U.S. Pat. No. 6,572,868, issued Jun. 3, 2003 to Sandra E. Cope, discloses a restructuring complex for cosmetic compositions. The composition comprises safe and effective amounts of carrageenans, borage seed oil, squalane, ceramide 3, ceramide 6, red algae extract, dipalmitoyl hydroxproline, and oleuropein. U.S. Pat. No. 6,193,987, issued Feb. 27, 2001 to M. H. Harbeck, discloses a lubricating composition for the hands and skin. The composition has as its constituents a mixture of organic safflower oil, flaxseed oil, tincture of benzoin, and organic beeswax. And, U.S. Pat. No. 6,479,043, issued Nov. 12, 2002 to Tietjen et al., discloses a depilatory composition. The composition includes emollients, skin conditioners, buffering agents, viscosity increasing agents, emulsion stabilizers, pH adjusters, chelating agents, fragrance, color, lubricants, propellants, or biological agents.

Various topical formulations and oral regimens of vitamins and herbs have been proposed for the treatment of skin conditions. U.S. Pat. No. 6,228,387, issued May 8, 2001 to M. Borod, describes a first composition for topical application and a second composition for oral administration for the treatment of hemorrhoids. The topical composition includes several herbs and vitamins, including grape seed extract and vitamin E, and in one embodiment, a few drops of Essential Oil of Chamomile. Vitamin E occurs naturally as a mixture of tocopherols, the most active being a-tocopherol, used externally, vitamin E is healing to the skin, being used for protection from sun damage, reducing facial lines and wrinkles, and improving skin smoothness, being used as an additive to massage oils and face creams.

In the prior art, there is little or no distinction between the production of the various compound used in the numerous skin treatments. The present invention provides for a combination of organic ingredients blended from various oils, waxes, extracts and minerals to provide an extended cell life cycle which makes for an exceptional anti-wrinkle formula that can be used everyday with no adverse side effects. The use of organic products, including wild crafted products eliminates additives such as synthetic preservatives and ingredients treated with chemical fertilizers. The products used in the blended compound do not contain genetically modified organisms, and are not processed using irradiation, industrial solvents, dyes, or chemical food additives. The combination of products has been found to produce a synergistic effect, increasing the useful properties of the individual compounds. By eliminating products that are made or produced with pesticides, genetically altered organisms or chemical fertilizers the effects of the product are enhanced and this limits any potential harmful side effects to the skin

BRIEF SUMMARY OF THE INVENTION

An organic skin moisturizer, which extends and improves the skin cells life cycle, comprised of Sea Buckthorn seed oil, Tamanu oil, Meadowfoam seed oil, Behenyl alcohol, Vetiver oil, Vitamin E or d-alpha tocopherol, Lecithin oil, Tea tree oil, *Helichrysum* oil, *Melissa* oil, and the titanium dioxide. The oils are blended together resulting in a compound that is easily applied to the skin for superior results to keep the skin cells healthier longer. This compound was created to address the Hayflick limit, which is that all skin cells can only divide a specific number of times before the skin cell dies.

The various components are added together to create the moisturizers. The various oils are blended at a controlled humidity. The oils are first filtered prior to blending. Application of the moisturizers should be done after the skin has been washed with a hot washcloth. The blended oils are applied to the fingertips or palm and applied in an upward motion to open the pores of the skin. If makeup or sun screen are to be applied after application of the moisturizer, then wait approximately 10 to 15 minutes or until the moisturizer has been absorbed by the skin

BRIEF DESCRIPTION OF THE SEVERAL VIEWS OF THE DRAWING

None

DETAILED DESCRIPTION OF THE INVENTION

Various embodiments of the invention will now be described. The following descriptions provide specific details for a thorough understanding and enabling description of these embodiments. Additionally, some well-known structures or functions may not be shown or described in detail, so as to avoid unnecessarily obscuring the relevant description of the various aspects and embodiments of the invention.

The terminology used in the description presented below is intended to be interpreted in its broadest reasonable manner, even though it is being used in conjunction with a detailed description of certain specific embodiments of the invention. Certain terms may even be emphasized herein; however, any terminology intended to be interpreted in any restricted manner will be overly and specifically defined as such in this Detailed Description section.

The present invention is a topical blended oil base created by combining numerous organically or naturally produced ingredients, most all of these ingredients are plant based. The various ingredients are oils that are blended and filtered to remove any non-essential impurities. By combining the various ingredients the applicant has found significant improvement in a user's skin. The skin is more youthful, firmer, softer, shows fewer wrinkles and increases the rate at which damaged skins is repaired. The present invention is a topical skin treatment that reduces dryness and removes or reduces fine wrinkles while aiding damaged skin heal itself. The present invention is beneficial to skin damaged from sunburns and radiation received during medical treatment. The moisturizer aids in the repair of damaged or blemished skin from exposure to a harsh environment, including; sun, wind, cold or dry environments or other environments that are damaging to the skin. The present invention produces a firmer tighter skin that is softer with fewer wrinkles and a more pleasing appearance.

The present invention is a skin moisturizers made of blended oils, waxes, extracts, roots, bark and at least one mineral. The present invention is not an emulsion and is not a water based moisturizer. The blended oil moisturizer discussed below uses primarily carrier, also known as fixed oils, and essential oils. The mixing of the two types of oils allows for the oils to be more readily blended and more readily absorbed into the skin. The ingredients in the moisturizers described below are made mostly from organic products and organic processing.

Essential oils are typically extracts from flower petals, root, bark, stem, leaves and other aromatic portions of the plant. There are several extraction methods in practice like the steam distillation method, cold-pressing method and solvent extraction method. The components of the claims presented in this application are derived from non-solvent extraction methods. These essential oils are thin oils with strong aromas. They are readily absorbed into the skin. The essential oils used in the present compound include, Vetiver essential oil, *Melissa* oil, Tea tree oil, and *Helichrysum* oil. All of these oils and there properties are known to those skilled in the art of manufacturing moisturizers and skin lotions.

Carrier oils, also called fixed oils, are vegetable oils that are used to dilute essential oils. Since essential oils can cause skin irritations or itching when used in undiluted forms. Carrier oils are used as base oils to dilute essential oils for maximum effectiveness. In the present compounds, the following oils are carrier oils; pomegranate seed oil, argan oil, sea buckthorn seed oil, and Tamanu oil, meadowfoam seed oil. The present invention is a moisturizer and skin repairer using the blended oils in a specific percent by volume. The inventor has found that the beneficial traits associated with the various components is enhanced using the volumes prescribed in the present invention. The components have synergistic effect when blended for a more enhanced result on the user's skin.

The moisturizers are produced using organic products, which means: the ingredients are grown and processed organically and screened for quality. For example, organic farming practices are designed to encourage soil and water conservation and reduce pollution. Farmers who grow organic produce don't use conventional methods to fertilize or control weeds. For example, rather than using chemical weed killers, organic farmers may conduct more sophisticated crop rotations and spread mulch or manure to keep weeds at bay. Additionally, the ingredients are organically processed which includes; cold press extraction or other means for processing the various plants to produces the oils without using or adding chemicals in the extraction process. Additionally, the various components are screened for quality including the testing for any abnormally high radiation which can be adsorbed into the various plants from fallout or naturally occurring isotopes found in various locals around the world. The ingredients are checked for radiation by a geiger counter and rejected if they measure above 60 counts per minute. The following moisturizers were developed using organic or natural ingredients and have produced exceptional results. The claims are not limited to organic ingredients but the applicant cannot confirm the same positive results using non-organic products.

The present invention is an organic damaged skin moisturizer comprised of approximately: 18-28% by volume Sea Buckthorn seed oil, also known as hippophae rhamnoides oil; 17-24% by volume Tamanu oil, also known as *Calophyllum Inophyllum*; 15-25% by volume Meadowfoam seed oil also known as *Limnanthes Alba* Seed Oil; 6-12% by volume Behenyl alcohol; 3-8% by volume Vitamin E, also known as d-alpha tocopherol; 2-8% by volume Lecithin oil; 2-8% by volume Tea tree oil also known as *Melaleuca Alternifolia* Leaf Oil; 1-5% by volume *Helichrysum* oil also known as *Helichrysum Italicum* Oil; 1-5% by volume *Melissa* oil also known as *Melissa Officinalis* oil; 2-15% by volume Vetiver oil also known as *Vetiveria zizaniodes*; and less than 1% by volume titanium dioxide.

Each ingredient is listed by their common name and their International Nomenclature of Cosmetic Ingredients, abbreviated INCI wherever possible. The INCI is a system of names for waxes, oils, pigments, chemicals, and other ingredients of soaps, cosmetics, and the like, based on scientific names and other Latin and English words.

The Sea Buckthorn seed oil is derived from the seed of the Hippophae rhamnoides a plant or shrub found throughout Europe and Asia. The oil is produced by cold press of the seeds and only the seeds which produces a number of fatty acids, including; Beta Carotene, Lycopene, Linoleic, Oleic, Palmitic, Palmitoleic, and Stearic acids. In addition to being used as a conditioning oil it is also beneficial in the treatment of burns, wounds, lesions, and sun damaged skin.

The Tamanu oil comes from the *Calophyllum inophyllum* which is a large evergreen tree. In Tahiti the tree is called the Tamanu tree and the desired oil is extracted from the kernel of the nut. The oil is a rich, thick green oil, however it is easily and completely absorbed into the skin. Once applied, it leaves the skin feeling smooth, plump and soft, with no greasiness, it also adds a healthy glow to the skin *Calophyllum* has a mild and pleasant aroma and can be easily mixed with most essential oils.

The Meadowfoam seed oil is extracted from the seeds of *Limnanthes alba* (meadowfoam). The seeds contain 20-30% oil. Meadowfoam seed oil is extraordinarily stable, primarily because it contains over 98% long chain fatty acids. Meadowfoam oil is used in cosmetic and hair-care applications due to its stability, lubricity and ability to stay on the skin.

The Behenyl alcohol is derived from corn and is an organic vegetable product used to thicken and stabilize the compound. It is often time used on cold sore or repairing damaged skin. The anti-septic aspect of this ingredient aids in the overall healing and repair of the user's skin.

The Vetiver oil, INCI name being *Vetiveria zizaniodes*, is an essential oil distilled from the roots of the *Chrysopogon zizanioides*. The plant is native to India but is cultivated throughout the tropical zones around the world. The oil has excellent fixative properties and is used widely in perfumes or other scented skin compounds. Vetiver oil is an Essential oil containing over 100 identified components. The oil is amber brown and rather thick. As it comes from the root of a swamp grass, the odor is described as deep, sweet, woody, smoky, earthy, amber, balsam and very strong.

Vitamin E, the INCI name being d-alpha tocopherol, is derived from vegetable oil and is used in various skin treatment and compound. D-alpha-tocopherol is an important lipid-soluble antioxidant and it protects cell membranes from oxidation by reacting with lipid radicals produced in the lipid peroxidation chain reaction. This process helps in removing free radical intermediates and prevent the oxidation reaction from continuing. The oxidized d-alpha-tocopheroxyl radicals produced in this process may be recycled back to the active reduced form through reduction by other antioxidants, such as ascorbate, retinol or ubiquinol.

Lecithin, the NCI name being Lecithin, can easily be extracted chemically or mechanically. It is usually available from sources such as soybeans, rapeseed, cottonseed, and sunflower. It has low solubility in water, but is an excellent emulsifier.

*Helichrysum* oil, the INCI name being *Helichrysum italicum* oil, which has properties that are beneficial to the skin, including; acting as an anti-inflammatory and soothes burns and raw chapped skin. It is used as a stabilizing and preserving agent in the present compound as well as a contributing to the benefits to the skin *Helichrysum* has been used in Europe for its healing qualities for over a millenia and is known as "imortelle" oil.

*Melissa* oil, the INCI name being *Melissa officinalis*, is derived from the plant *Melissa officinalis*. This oil has been used in aroma therapy for centuries the healing and soothing aspect of this ingredient assists the overall repair and moisturizing of the skin.

The Tea Tree oil, the NCI name being *Melaleuca Alternifolia* Leaf Oil, contributes to the stability of the blended oils and are high in antioxidants.

Titanium dioxide is a powdered mineral added to the compound to increase protection of the skin from ultra violet light and increases the shelf life of the compound as an antioxidant, reducing the oxidations of the organic compound.

The damaged skin moisturizer has a strong pungent smell and is applied topically and allowed to sit on the skin for at least 8 hours.

I claim:
1. A skin moisturizer comprising:
   18-25% by volume Sea Buckthorn seed oil, the INCI name being hippohae rhamnoides oil;
   15-25% by volume Tamanu oil, the INCI name being *Calophyllum Inophyllum* oil;
   18-28%, by volume Meadowfoam seed oil, the INCI name being *Limnanthes alba* seed oil;
   5-15% by volume Behenyl alcohol;
   2-15% by volume Vetiver oil, the INCI name being *Vetiveria zizaniodes;*
   3-8% by volume Vitamin E, the INCI name being d-alpha tocopherol;
   2-8% by volume Lecithin oil, the INCI name being Lecithin;
   1-5% *Helichrysum* oil, the INCI name being *Helichrysum italicum* oil;
   1-5% by volume *Melissa* oil, the INCI name being *Melissa officinalis* oil;
   less than 3% by volume Tea tree oil, the INCI name being *Melaleuca Alternifolia* Leaf Oil; and
   less than 1% titanium dioxide.

\* \* \* \* \*